United States Patent [19]

Caulkett et al.

[11] Patent Number: 5,246,932
[45] Date of Patent: Sep. 21, 1993

[54] HETEROCYCLIC COMPOUNDS

[75] Inventors: Peter W. R. Caulkett; Geraint Jones, both of Macclesfield; Michael G. Collis, Barham; Simon M. Poucher, Handforth, all of England

[73] Assignee: Imperial Chemical Industries PLC, Great Britain

[21] Appl. No.: 887,211

[22] Filed: May 21, 1992

[30] Foreign Application Priority Data

May 23, 1991 [GB] United Kingdom ................ 9111131

[51] Int. Cl.$^5$ ................ C07D 519/00; C07D 405/14; A61K 31/53
[52] U.S. Cl. .................................. 514/245; 544/212; 544/198; 544/207; 544/209
[58] Field of Search ............... 544/212, 198, 207, 209; 514/245

[56] References Cited

U.S. PATENT DOCUMENTS

| | | | |
|---|---|---|---|
| 3,846,423 | 11/1974 | Kobe et al. | 260/248 |
| 3,995,039 | 11/1976 | Rooney et al. | 424/249 |
| 4,133,674 | 1/1979 | Cartwright et al. | 71/93 |
| 4,560,689 | 12/1985 | Yokoyama | 514/250 |
| 4,713,383 | 12/1987 | Francis et al. | 514/267 |
| 4,734,413 | 3/1988 | Wade | 514/222 |

FOREIGN PATENT DOCUMENTS

| | | |
|---|---|---|
| 815405 | 11/1974 | Belgium . |
| 0172608 | 2/1986 | European Pat. Off. . |
| 0207651 | 1/1987 | European Pat. Off. . |
| 0217748 | 4/1987 | European Pat. Off. . |
| 0263071 | 4/1988 | European Pat. Off. . |
| 0374808 | 6/1990 | European Pat. Off. . |
| 0383589 | 8/1990 | European Pat. Off. . |
| 0459702 | 12/1991 | European Pat. Off. . |
| 2720792 | 11/1977 | Fed. Rep. of Germany . |
| 743316 | 7/1974 | South Africa . |
| 2016002 | 9/1979 | United Kingdom . |
| 2134107 | 8/1984 | United Kingdom . |

OTHER PUBLICATIONS

Callis, et al. "Inhibition of Renal Vasoconstriction Induced by Intrarenal Hypertonic Sailne by the Nonxanthine Adenosine Antagonist CGS 15943A" *J. Pharmacol Exp. Therap* (1989), 248, 1123-1129.

(List continued on next page.)

*Primary Examiner*—John M. Ford
*Attorney, Agent, or Firm*—Cushman, Darby & Cushman

[57] ABSTRACT

A compound of the formula I

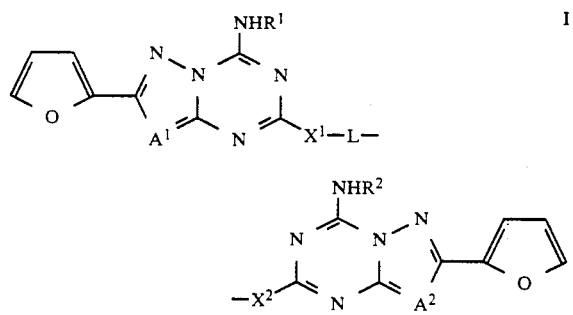

wherein:

$A^1$ and $A^2$ are each independently N or CT in which T is hydrogen or (1-4C)alkyl;

$R^1$ and $R^2$ are each independently hydrogen, (1-6C)alkyl, or (1-4C)alkanoyl;

$X^1$ and $X^2$ are each independently O, S or NH; and

L is a (3-7C)cycloalkylene group or a (1-8C)alkylene chain optionally interrupted or extended by a group selected from phenylene, phenyleneoxy or oxyphenyleneoxy, the phenylene portion of said group being unsubstituted or substituted by one of halogen, hydroxy and (1-4C)alkoxy, provided that all heteroatoms in the group $X^1$—L—$X^2$ are separated from one another by at least two carbon atoms; or a pharmaceutically acceptable salt thereof, processes for preparing the compounds and pharmaceutical compositions containing them. The compounds are useful as adenosine antagonists.

9 Claims, No Drawings

OTHER PUBLICATIONS

E. B. Akerblom, D. E. S. Campbell "Nitrofuryltriazole Derivatives as Potential Urinary Tract Antibacterial Agents" *J. Med. Chem.* (1973), 16, 312–319.

W. Ried, S. Aboul-Fetouh "Synthesis of New Substituted Pyrazolo[1,5-a]pyrimidines and Pyrazolo[1,5-a]-1,3,5-Triazines" *Tetrahedron* (1988), 44, 7155–7162.

J. P. Miller, et al. "Inhibition of Cyclic AMP Phosphodiesterases by Cyclic Nucleotide Analogs and Nitrogen Heterocycles" *Advances in Cyclic Nucleotide and Protein Phosphorylation Research* (1984), 16, 277–290.

K. Senga, et al. "Synthesis and Enzymic Activity of Various Substituted Pyrazolo[1,5-a]-1,3,5-triazines as Adenosine Cyclic 3',5'-Phosphate Phosphodiesterase Inhibotors" *J. Med. Chem.* (1982), 25, 243–249.

G. Griebel, et al. "Behavioural effects of Selective $A_2$ Adenosine Receptor Antagonists, CGS 21197 and CGS 22706, in Mice" *NeuroReport* (1991), 2, 139–140.

S. P. Langdon, et al. "Triazines and Related Products. Part 26. Synthesis and Chemistry of Bicyclic Analogs of the Antitumor Drug 2,4,6-Tris(dimethylamino)-1,3,5-triazine (Hexamethylmelamine)" *J. Chem. Soc., Perkin Trans I* (1984), 993–998.

HETEROCYCLIC COMPOUNDS

This invention concerns novel heterocyclic compounds and, more particularly, certain 2-furyl-triazolo[1,5-a][1,3,5]triazines and pyrazolo[2,3-a][1,3,5]triazines which have useful pharmacological properties (and in particular antagonise the actions of adenosine such as vasodilation). The invention also includes pharmaceutical compositions containing the novel azole derivatives for use in treating certain diseases and disorders affecting mammalian cardiac, peripheral and/or cerebral vascular systems. Also included are processes for the manufacture and formulation of the novel azole derivatives.

The compound theophylline (1,3-dimethylxanthine) has been used clinically (usually as its ethylene diamine salt, which is also known as aminophylline) as a respiratory stimulant, a centrally acting stimulant, a bronchodilator, a cardiac stimulant and as a diuretic. This diversity of clinical uses is an indication of the range of pharmacological actions which have been attributed to theophylline. These include phosphodiesterase inhibition, adenosine receptor antagonism, mobilisation of intracellular calcium and the release of catecholamines. Recently theophylline has also been reported to be useful in treating myocardial ischaemia (Maseri et al., *The Lancet*, 1989, 683-686), skeletal muscle ischaemia (Picano et al., *Angiology*, 1989, in press) and cerebral ischaemia (Skinhoj et al., *Acta. Neurol. Scand.*, 1970, 46, 129-140). The beneficial effects of theophylline in these ischaemic disorders are believed to be due to a reduction or prevention of the phenomenon known as "vascular steal" by virtue of the compound's ability to antagonise the actions of adenosine by blocking the adenosine receptors which mediate metabolism-linked vasodilatation.

The "vascular steal" phenomenon can occur when the major artery supplying a particular vascular bed is partially or totally occluded resulting in ischaemia. In this situation, the compromised vascular bed dilates and blood flow is maintained by either an increase in flow across the narrowed vessel or by an increase in flow through the collateral vessels. However, increased metabolic activity in adjacent vascular beds results in release of mediators such as adenosine, causing them to dilate, resulting in the limited blood flow to the compromised vascular bed being "stolen" by these adjacent areas. The loss of blood from compromised to normally perfused vascular beds by the phenomenon of "vascular steal" further diminishes the blood flow in the compromised vascular bed.

The diversity of pharmacological properties possessed by theophylline make it difficult to use in the regular treatment or prevention of occlusive diseases and conditions of the vasculature. Thus, its associated action as a phosphodiesterase inhibitor results in cardiac stimulation which is deleterious for patients with myocardial ischaemia. Furthermore, the relatively low potency of theophylline means that dose-levels which are therapeutically useful are close to those which can cause serious central side-effects.

European patent application publication no. EP A2 383589 discloses the formulae of certain 2-furyl-pyrazolo[2,3-a][1,3,5]triazines, although no details of their preparation are given. No therapeutic use is ascribed to any of these compounds.

Several triazolo[1,5-a][1,3,5]triazines and pyrazolo[2,3-a][1,3,5]triazines which do not have a 2-furyl substituent, have been ascribed therapeutic uses. Thus, certain triazolo[1,5-a][1,3,5]triazines have been disclosed as bronchodilators (see U.S. Pat. No. 4,734,413). Certain pyrazolo[2,3-a][1,3,5]triazines have been disclosed variously as inhibitors of gastric acid secretion (see British patent application publication no. 2134107 and European patent application publication no. EP A2 0172608); as antiinflammatory agents (see European patent applications publication nos. EP A2 0172608 and EP A2 207651); as bronchodilators (see British patent application publication no. GB 2016002, Belgian patent no. 815405 and U.S. Pat. No. 3,995,039), and as phosphodiesterase inhibitors (see U.S. Pat. No. 3,846,423 and J. Med. Chem., 1982, 25(3), 243-9).

European patent application publication no. EP A1 459702, published on Dec. 4, 1991 discloses certain 2-heteroaryltriazolo[1,5-a][1,3,5]triazines and pyrazolo[2,3-a][1,3,5]triazines having adenosine antagonist activity.

We have now discovered (and this is a basis for our invention) that a group of novel 2-furyl-triazolo[1,5-a][1,3,5]triazines and pyrazolo[2,3-a][1,3,5]triazines of formula I defined below are effective antagonists of the actions of adenosine and in particular of its vasodilatory actions.

According to the invention there is provided a compound of the formula I set out hereinafter (together with the other formulae appearing in Roman numerals) wherein:

$A^1$ and $A^2$ are each independently N or CT in which T is hydrogen or (1-4C)alkyl;

$R^1$ and $R^2$ are each independently hydrogen, (1-6C)alkyl, or (1-4C)alkanoyl;

$X^1$ and $X^2$ are each independently O, S or NH; and

L is a (3-7C)cycloalkylene group or a (1-8C)alkylene chain optionally interrupted or extended by a group selected from phenylene, phenyleneoxy or oxyphenyleneoxy, the phenylene portion of said group being unsubstituted or substituted by one of halogen, hydroxy and (1-4C)alkoxy, provided that all heteroatoms in the group $X^1$—L—$X^2$ are separated from one another by at least two carbon atoms; or a pharmaceutically acceptable salt thereof.

It will be appreciated that certain of the compounds of formula I may exist in and be isolated in one or more different enantiomeric or racemic forms (or mixtures thereof). It is to be understood that the invention includes any of such forms which possesses the property of antagonising the actions of adenosine, it being well known how to prepare individual enantiomeric forms, for example, by synthesis from appropriate chiral starting materials or by resolution of a racemic form. Similarly, the adenosine antagonist properties of a particular form may be readily evaluated, for example by use of one or more of the standard in vitro or in vivo screening tests detailed hereinbelow.

$R^1$ and $R^2$ may each independently be, for example, hydrogen, methyl or acetyl. Preferably $R^1$ and $R^2$ are both hydrogen.

$A^1$ and $A^2$ may each independently be, for example, N or CT in which T is hydrogen or methyl. Preferably $A^1$ and $A^2$ are N or CH. For example, $A^1$ and $A^2$ may both represent N or both represent CH.

Preferably one of $X^1$ and $X^2$ represents S or NH, more preferably NH. The other of $X^1$ and $X^2$ may represent O, S or NH, but preferably represents O or NH. For example, one of $X^1$ and $X^2$ may represent NH and the other O.

When L represents a (3–7C)cycloalkylene group, it may be for example, a cyclopentylene or cyclohexylene group, such as a 1,4-cyclohexylene group.

When L represents a (1–8C)alkylene chain optionally interrupted or extended by a phenylene, phenyleneoxy or oxyphenyleneoxy group, the alkylene chain may be branched or unbranched, as for example in methylene, ethylene, propylene, methylethylene, butylene, dimethylethylene, pentylene or hexylene.

When L represents a (1–8C)alkylene chain that is interrupted or extended by a phenylene, phenyleneoxy or oxyphenyleneoxy group, it may be, for example, ethylenephenyleneethylene, ethylenephenyleneoxyethylene, ethyleneoxyphenyleneoxyethylene, phenylenemethylene, phenyleneethylene or phenyleneoxyethylene, the phenylene portion of any of which may be unsubstituted or substituted by one of halogen, hydroxy and (1–4C)alkoxy. The phenylene portion may be 2-, 3- or 4-phenylene, as for example in ethylene(2-phenylene)ethylene, methylene(3-phenylene)ethylene, 2-phenyleneethylene, 3-phenyleneethylene or 4-phenyleneethylene. It will be appreciated that the alkylene chain may not be extended by an oxyphenyleneoxy group, since an oxygen atom in L would then not be separated from $X^1$ or $X^2$ by at least two carbon atoms.

When L represents a (1–8C)alkylene chain that is not interrupted or extended, it may be, for example, an ethylene, propylene, butylene, pentylene or hexylene group. It will be appreciated that L may not represent a methylene group, since the two heteroatoms $X^1$ and $X^2$ would then be separated by only one carbon atom.

Particular examples of substituents which may be present on phenyl are:

for halogen: fluorine and chlorine;

hydroxy, and for (1–4C)alkoxy: methoxy or ethoxy.

A group of compounds of particular interest comprises those compounds in which:

$R^1$ and $R^2$ are both hydrogen;

$A^1$ and $A^2$ are each independently N or CH;

$X^1$ is O;

$X^2$ is S or NH; and

L is a phenylene(1–3C)alkylene or phenyleneoxy(-2–3C)alkylene group, the phenylene portion of said group being unsubstituted or substituted by one of halogen, hydroxy and (1–4C)alkoxy; and pharmaceutically acceptable salts thereof.

Of these compounds of particular interest, mention may be made of those in which $A^1$ and $A^2$ both represent N. Mention may also be made of those wherein $X^2$ is NH. Further mention may be made of those wherein L is 4-phenylenemethylene, 4-phenyleneethylene, 3-phenyleneethylene, 2-phenyleneethylene, 1-(4-phenylene)-2,2-dimethylethylene and 4-phenyleneoxyethylene.

Particular pharmaceutically acceptable salts include, for example, salts with acids affording physiologically acceptable anions, for example, salts with strong acids, such as hydrochloric, hydrobromic, sulphuric, phosphoric, methanesulphonic and trifluoracetic acids. In addition, for those compounds of formula I which are sufficiently basic, suitable salts include, for example, salts with organic acids affording a physiologically acceptable anion such as salts with oxalic, citric or maleic acid. Certain compounds of formula I, for example those in which L comprises a hydroxy-substituted phenylene group, may form base salts with bases affording physiologically acceptable cations, such as alkali metal and alkaline earth metal salts.

The compounds of formula I may be manufactured using procedures analogous to those well known in the arts of heterocyclic and organic chemistry for the production of structurally analogous compounds. Such procedures are included as a further feature of the invention and include the following preferred procedures for the manufacture of a compound of the formula I in which $R^1$, $R^2$, $A^1$, $A^2$, $X^1$ and $X^2$ have any of the meanings defined above:

(a) The reaction of a compound of the formula II in which Z is a suitable leaving group, for example hydrocarbylsulphonyl such as (1–6C)alkylsulphonyl (such as methylsulphonyl or ethylsulphonyl), arylsulphonyl (such as phenylsulphonyl), aryloxy such as phenoxy or halogeno (such as chloro or bromo), with a compound of the formula III.

The process is generally carried out under basic conditions. These may be conveniently provided by the inherent basicity of the reactants, for example when $X^1$ is amino. Alternatively, the basic conditions may be provided by adding a suitable base to the reaction mixture. Suitable bases include, for example, tertiary amines such as trimethylamine, triethylamine, pyridine, 2,6-dimethylpyridine and 1,8-diazabicyclo[5.4.0]undec-7-ene. It will be appreciated that the basic conditions may also be provided by using the compound of the formula III in the form of a salt such as an alkali metal salt, for example, a lithium, sodium or potassium salt. Such a salt may be prepared separately, or formed in situ immediately prior to the above process (a), by any conventional method, for example by reacting the compound of the formula III with an alkali metal (1–4C)alkoxide, hydroxide or hydride in a suitable solvent or diluent such as acetonitrile, 1,2,-dimethoxyethane, t-butyl methyl ether, tetrahydrofuran, ethanol or N,N-dimethylformamide.

The process (a) will generally be performed at a temperature in the range, for example, 10° to 120° C. and conveniently in the range 30° to 90° C. and in a suitable solvent or diluent such as acetonitrile, ethanol, tetrahydrofuran, 1,2-dimethoxyethane, t-butyl methyl ether or N,N-dimethylformamide.

The starting materials of formula II may be obtained by standard procedures well known in the art. Thus, for example, those compounds of formula II in which Z is hydrocarbylsulphonyl may be made by oxidation of the corresponding hydrocarbylthio derivative of formula IV in which $R^3$ is hydrocarbylthio, using a conventional oxidant such as a peracid, for example, peracetic, perbenzoic or chloroperbenzoic acid, conveniently at a temperature in the range, for example, 0° to 40° C., and in a suitable solvent or diluent such as dichloromethane or chloroform. Similarly, those compounds of the formula II in which Z is chloro or bromo may be obtained, for example, by reacting a hydrocarbylthio derivative of formula IV (especially in which $R^3$ is methylthio or ethylthio) with chlorine or bromine in the presence of hydrogen chloride or hydrogen bromide, respectively, at a temperature in the general range, for example, −20° to 15° C. and in a generally inert polar solvent such as ethanol or 2-propanol. The compounds in which Z is aryloxy may be prepared from the corresponding compounds in which Z is hydrocarbylsulphonyl by reaction with a phenol in the presence of a base.

The starting hydrocarbylthio starting materials of formula IV may themselves be obtained, for example, by reaction of a compound of the formula V with the appropriate dihydrocarbyl N-cyanodithioiminocarbonate of formula VI, in which $R^3$ has any of the meanings defined above, at elevated temperature in the range, for example, 60° to 200° C., conveniently as a melt in the absence of solvent or diluent, to give the compound of formula IV in which $R^1$ is hydrogen. When a compound of formula I in which $R^1$ is alkyl or alkanoyl is required, the compound of formula IV in which $R^1$ is hydrogen may be alkylated or acylated in conventional manner.

The starting compounds of formula V wherein $A^1$ is N may themselves be obtained, for example by reacting the appropriate iminoether of the formula Q.C(OR)=NH in which Q is 2-furyl and R is (1-4C)alkyl such as methyl or ethyl (formed from the corresponding nitrile of the formula Q.CN and alcohol of the formula R.OH in the presence of an anhydrous acid such as hydrogen chloride) with an aminoguanidine salt (especially the nitrate) in the presence of a suitable base, such as pyridine or 2,6-lutidine, which may also be used as the reaction solvent, at a temperature in the range, for example, 60°-120° C.

The starting compounds of formula V wherein $A^1$ is CT may themselves be obtained, for example by reacting the appropriate ester of the formula Q.CO₂R (in which Q is 2-furyl and R is lower alkyl such as methyl or ethyl) under basic conditions with an alkali metal salt of the formula T.CHM.CN (in which M is an alkali metal such as sodium or lithium), conveniently produced in situ by adding a nitrile of the formula T.CH₂.CN to a solution of the alkali metal in liquid ammonia, to give the corresponding cyanoalkylketone of the formula Q.CO.CH(T).CN. The latter compound is then cyclised with hydrazine, for example by heating in a suitable solvent or diluent such as ethanol or propanol to give the required pyrazole of formula V.

The compounds of formula III may be prepared by reacting a compound of formula II with a compound of formula $HX^1.L.X^2H$ or a corresponding derivative in which $X^1$ is protected, for example with a benzyl group. Since the compounds of formula II are also starting materials in process a) above, it will be understood that in process a), the compounds of formula III may be generated in situ. When the compound of formula III is to be generated in situ, the molar ratio of the compound of formula II to the compound of formula $HX^1.L.X^2H$ employed is conveniently about two. When the compound of formula III is prepared using a protected derivative of a compound of formula $HX^1.L.X^2H$, the protecting group will have to be removed. For example, a benzyl group may be removed by hydrogenation.

(b) For those compounds of formula I in which L contains a phenylene moiety which is substituted by a hydroxyl group, a corresponding derivative of formula I in which the hydroxy group is protected, for example with a benzyl group, is deprotected.

The protecting group and deprotection conditions are those well known in the art for use with hydroxy groups and which are compatible with the presence of other reactive groups in the formula I compound. Thus, for example, a benzyl group may be removed by hydrogenation in the presence of a suitable catalyst such as palladium-on-carbon at or about atmospheric pressure of hydrogen in a suitable inert diluent or solvent such as methanol, ethanol or t-butyl methyl ether and at or about ambient temperature.

The protected derivatives of formula I may in general be made using analogous procedures to process (a) herein but starting from the appropriately protected starting materials.

It will be appreciated that those compounds in which $R^1$ and/or $R^2$ are other than hydrogen may also be obtained by carrying out a conventional alkylation or acylation of the corresponding formula I compound in which $R^1$ and/or $R^2$ is hydrogen obtained by process (a) above.

Whereafter, when a pharmaceutically acceptable salt is required, it may be obtained, for example, by reacting a compound of formula I with the appropriate acid or base affording a physiologically acceptable ion or another conventional procedure.

Similarly, when an optically active form of a chiral compound of formula I is required, either process (a) or (b) above may be carried out using the appropriate optically active starting material or else a racemic form may be resolved by a conventional procedure, for example, using an optically active form of a suitable acid.

As stated above, the compounds of the invention possess the property of antagonising one or more of the physiological actions of adenosine and are valuable in the treatment of diseases and medical conditions affecting the mammalian cardiac, peripheral and/or cerebral vascular systems, such as ischaemic heart disease, peripheral vascular disease (claudication) and cerebral ischaemia. The compounds may also be useful in the treatment of migraine.

The effects of compounds of formula I as adenosine receptor antagonists may be demonstrated in one or more of the following standard in vitro and/or in vivo tests.

(a) $A_2$ Adenosine receptor affinity test

This test involves the ability of a test adenosine antagonist to displace the known adenosine mimetic agent [$^3$H]-N-ethylcarboxamidoadenosine (NECA) from binding sites on membrane preparations derived from the rat phaeochromocytoma cell line PC 12 (available from the Beatson Institute, Glasgow). The basic procedure has been described by Williams et al. (*J. Neurochemistry*, 1987, 48(2), 498–502).

The membrane preparation is obtained as follows: Frozen pellets of PC12 cells are washed twice with ice cold, buffered, physiological saline and the cells recovered by centrifugation (1500G) at 3° C. The separated cells are then suspended in hypotonic solution (distilled water), allowed to stand on ice for 30 minutes and are then carefully homogenized using a standard high-speed homogeniser with periodic ice-cooling to obtain a fine suspension. The homogenate is centrifuged (48000G) and the pellet is resuspended in 50 mM tris-HCl buffer, pH 7.4 containing adenosine deaminase (5 units/ml, Type IV from calf intestinal mucosa, available from Sigma Chemical Corporation, under reference no. A1280). The mixture is then incubated at 37° C. After 20 minutes, the reaction is terminated by dilution with ice-cold buffer and transfer onto ice. The material obtained containing the cell membranes is recovered by centrifugation and washed by resuspension in buffer and recentrifugation. The pellet produced is then resuspended in ice-cold buffer using a hand-driven homogenizer. The resultant membrane suspension is frozen and stored under liquid nitrogen until required.

Binding studies are carried out in microtitre plates, the assay mixtures being buffered in 50 mM tris-HCl, pH 7.4 at room temperature. The test compound is dissolved in dimethyl sulphoxide (DMSO) and then diluted with assay buffer to give the test solutions. [The final concentration of DMSO is not allowed to exceed 1% by volume, at which level it does not affect radioligand binding to the membrane receptor.] Incubations are performed at 30° C. for 90 minutes in a total volume of 150 μl comprising the test solution or buffer (50 μl), tritiated NECA (50 μl) and membrane suspension (50 μl). After incubation, the samples are rapidly filtered over glass-fibre mats and the filter mats are washed to remove non-receptor-bound radioligand. Receptor-bound radioligand entrapped on the filter mats is then determined by liquid scintillation counting. Filtration and washing are carried out using a conventional vacuum filtration cell harvester. The specific binding (defined as the difference between the total binding and the non-specific binding) in the presence of the particular test compound is determined and compared with the control value. Results are conveniently expressed as the negative logarithm of the concentration required to cause a 50% displacement of control specific binding ($pIC_{50}$).

In general, compounds of the formula I showing antagonist activity in this assay typically show a $pIC_{50}$ in the above test (a) of 6 or more. Thus for example, the compound of Example 1 herein shows a $pIC_{50}$ of about 9.1. Using the same test procedure, the known compound 1,3-dimethylxanthine typically shows a $pIC_{50}$ of about 5.

(b) Guinea-pig Aortic Constriction Test

This test has been described by Collis et al. (*British J. Pharmacology*, 1989, 97, 1274–1278) and involves the assessment of the ability of a test compound to antagonise the attenuatory effect of adenosine on phenylephrine induced constriction of a guinea-pig aortic ring preparation, an effect mediated via the adenosine receptor known as $A_2$.

The aortic ring preparation is obtained as follows:- Sections (3-5 mm) of guinea pig thoracic aorta (from Dunkin Hartley strain, 250–400 g males) are mounted in organ baths containing oxygenated Krebs solution (95% $O_2$: 5% $CO_2$) at 37° C. [The nucleoside transport inhibitor, dipyridamole (10 μM) is present in the Krebs solution]. The isometric tension development is recorded and the tissue placed under a resting tension of 1 g and allowed to equilibrate for 1 hour. The aortic ring preparation is then sensitised to $10^{-5}$M phenylephrine. Erythro-9-(2-hydroxy-3-nonyl)adenine (EHNA) (10 μM) is added to the preparation and after 10 minutes the tissue is constricted to approximately 50% maximum by adding $3 \times 10^{-6}$M phenylephrine. Adenosine is next added cumulatively ($10^{-7}$M to $10^{-3}$M) and the evoked relaxation is measured. After washout for 20 minutes, a $10^{-5}$M solution of the test compound in DMSO (maximum 1% by volume) diluted with Krebs solution is added and left to equilibrate for 30 minutes. Twenty minutes into the equilibration period further EHNA (10 μM) is added to the preparation and 10 minutes later phenylephrine ($3 \times 10^{-6}$M) is introduced to produce constrictive tone again. A repeat dose response curve to adenosine is then carried out followed by washout.

Test compounds are assessed by plotting the percentage relaxation observed against the logarithm of the adenosine concentration, competitive adenosine antagonism producing a parallel shift in the standard adenosine concentration/relaxation (dose response) curve. The dose ratio (DR) is calculated from the ratio of the concentration of adenosine to produce a 50% relaxation ($ED_{50}$) in the presence of the test antagonist divided by the $ED_{50}$ concentration of adenosine in the absence of the test antagonist for each aortic ring. Significant antagonist activity in this assay is indicated by a DR of >2. The pA2 value, which is an estimate of the concentration of antagonist to give a dose ratio of 2, may also be calculated using a standard computation technique. Using this test procedure the known compound, 1,3-dimethylxanthine, has a pA2 of about 5.

(c) Guinea-pig Atrial Bradycardic Test

This test has also been described by Collis et al. (*British J. Pharmacology*, 1989, 97, 1274–1278) and involves the ability of a test compound to antagonise the bradycardic effect of the adenosine mimetic, 2-chloroadenosine, in a beating guinea-pig atrial preparation, an effect mediated via the adenosine receptor known as $A_1$.

The atrial pair preparation may be obtained as follows: Atrial pairs are obtained from guinea-pigs (Dunkin Hartley strain, 250-400 g males) and mounted in organ baths containing oxygenated Krebs buffer solution (95% $O_2$; 5% $CO_2$) at 37° C. The spontaneously beating atria are then placed under a resting tension of 1 g and allowed to equilibrate for 50 minutes with continuous overflow. Overflow is then stopped and adenosine deaminase (1 Unit/ml) added to prevent the accumulation of endogenously produced adenosine. After equilibration for 15 minutes, a cumulative dose response curve to the adenosine mimetic, 2-chloroadenosine ($10^{-8}$M to $10^{-4}$M) is administered to produce a maximal slowing of atrial rate. After washout during 30 minutes, adenosine deaminase is readministered to the bath which is allowed to equilibrate for 15 minutes. A $10^{-5}$M solution of the test compound in DMSO is then added to the bath which is left to incubate for 30 minutes. Any effect on the beating rate due to the test compound is noted before the dose response curve to 2-chloroadenosine is repeated. Compounds which are adenosine antagonists attenuate the 2-chloroadenosine response.

Test compounds are assessed by comparing dose response curves to 2-chloroadenosine alone with those obtained in the presence of the compound. Competitive adenosine antagonists produce a parallel shift in the 2-chloroadenosine dose response curve. The dose ratio (DR) is calculated from the ratio of the concentration of 2-chloroadenosine to produce a 50% reduction in atrial rate ($ED_{50}$) in the presence of the test compound divided by the $ED_{50}$ concentration of 2-chloroadenosine in the absence of the test compound for each atrial pair. The pA2 is then obtained in an analogous manner to that referred to in (b) above. In this test, the compound of Example 1 herein has a pA2 of 6.0. Similarly, the known compound, 1,3-dimethylxanthine, typically shows a pA2 of about 5.

(d) Anaesthetised cat blood pressure Test

This test assesses the ability of a test compound to antagonise the fall in diastolic blood pressure produced by administration of the adenosine mimetic, 2-chloroadenosine.

Male cats (2-3 kg) are anaesthetised with sodium pentobarbitone (45 mg/kg, ip). The following blood vessels are catheterised: right jugular vein (for infusion of the anaesthetic at approximately 7 mg/kg per hour as a 3 mg/ml solution in isotonic saline), the left jugular vein (for administration of test agents) and the right common carotid artery (for monitoring blood pressure and pulse rate). The blood gas status and pH are determined, and are maintained within physiological limits, before administration of 2-chloroadenosine. A control dose response curve (DRC) to 2-chloroadenosine (0.3 to 30 μg/kg) against the fall in diastolic blood pressure is determined. A solution of the test compound in a mixture of 50% v/v polyethylene glycol (PEG) 400 and 0.1M sodium hydroxide is then administered i.v. and after 15 minutes the DRC to 2-chloroadenosine is determined. This procedure is repeated twice with blood gases and pH being monitored and maintained within physiological limits between each DRC. The concentration of 2-chloroadenosine required to cause a 30 mm Hg fall in diastolic blood pressure is then calculated for each dose of test compound and a Schild plot constructed for those which produce a dose ratio (DR) of >2. From this plot a $K_B$ value is determined.

The above Test (d) may conveniently be modified to allow evaluation of orally administered test compounds by administering the test compound to conscious cats with indwelling arterial and venous catheters and measuring the effect in preventing an adenosine induced decrease in blood pressure.

(e) Anaesthetised dog Test

This test involves the assessment of the effects of a test compound on antagonising the actions of adenosine in lowering heart rate and increasing vasodilation (as measured by a fall in hind-limb perfusion pressure).

Beagles (12-18 kg) are anaesthetised with sodium pentobarbitone (50 mg/kg, iv). The following blood vessels are catheterised: right jugular vein (for infusion of the anaesthetic at approximately 112 mg per hour as a 3 mg/ml solution in isotonic saline), right brachial vein (for administration of drugs and test agents), right brachial artery (for measurement of systemic blood pressure and pulse rate) and the left carotid artery (for administration of adenosine into the left ventricle). Both vagi, the right femoral and sciatic nerves are ligated and severed. A bolus injection of 1250 U heparin is administered before perfusing the right hindlimb at constant blood flow with blood from the iliac artery. The right leg is tied just below the ankle. Xamoterol (1 mg/kg) is then administered to the animal to stabilise heart rate at a high level and nitrobenzylthioinosine (NBTI, 0.5 mg/kg) to inhibit the uptake of adenosine. The animal is sensitised to adenosine during the equilibration time following NBTI by carrying out a dose response curve (DRC). During this time any blood gas or pH imbalance is corrected. A control DRC is performed followed by up to three DRC's after cumulative administration of the test compound (as described in (d) above). Each DRC is carried out 15 minutes after administration of test compound and after the measured parameters of heart rate and hindlimb perfusion pressure have returned to a stable state. Similarly, blood gases and pH are maintained within physiological limits throughout the evaluation.

The amount of adenosine required to cause a 50% fall in measured parameter ($ED_{50}$) i.e. heart rate and hindlimb perfusion pressure is calculated for each does of test compound and a Schild plot constructed. From this plot a $K_B$ value is determined for antagonism of heart rate response and vasodilator response to adenosine.

f) Anaesthetised cat exercise hyperaemia test

This test involves assessment of the effect of a test compound to antagonise the vasodilation response which occurs during twitch contraction of skeletal muscle. The vasodilation is mediated partly by the release of endogenous adenosine from the contracting skeletal muscle.

Cats (2.4-3.6 kg) are anaesthetised with sodium pentobarbitone (50 mg.kg$^{-1}$ ip). The following blood vessels are catheterized: left jugular vein (for infusion of anaesthetic, at approximately 0.12 mg$^{-1}$ min$^{-1}$ as a 6 mg.ml$^{-1}$ solution in isotonic saline), right external jugular vein (for administration of drugs and test compounds), right common carotid artery (for measurement of systemic arterial blood pressure and pulse rate) and right brachial artery (for withdrawal of blood).

Blood flow to the left hind limb is measured with an electromagnetic flow probe around the left external iliac artery. The whole of the left hind limb is made to contract at 3 Hz for 20 minutes duration by stimulating the sciatic and femoral nerves. Active tension produced by the extensor digitorum longus and peroneous longus muscles is measured isometrically with a force transducer. Exercise is repeated twice within the same animal, in either the absence or presence of the test compound. Test compounds are assessed for their ability to reduce the vasodilatation during skeletal muscle contraction.

In this test, the known compound, 1,3-dimethylxanthine, produces significant inhibition at 10 mg.kg$^{-1}$.

In general, the majority of compounds of formula I show activity as adenosine antagonists which is predominantly selective for adenosine $A_2$ receptors.

The compounds of the invention are generally best administered to warm-blooded animals for therapeutic or prophylactic purposes in the treatment or prevention of cardiovascular diseases and adverse conditions in the form of a pharmaceutical composition comprising said compound of formula I or a pharmaceutically acceptable salt thereof and a pharmaceutically acceptable diluent or carrier. Such compositions are provided as a further feature of the invention.

In general, it is envisaged that a compound of formula I will be administered orally, intravenously or by some other medically acceptable route (such as by inhalation, insufflation, sub-lingual or transdermal means) so that a dose in the general range, for example, 0.001 mg to 10 (and more particularly in the range, for example, 0.05 to 5 mg/kg) mg/kg body weight is received. However, it will be understood that the precise dose administered will necessarily vary according to the nature and severity of the disease or condition being treated and on the age and sex of the patient.

A composition according to the invention may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; in the form of a powder, together with pharmaceutically acceptable inert solid diluents such as lactose, for administration by insufflation; or in the form of a skin patch for transdermal administration. The compositions may conveniently be in unit dose from containing, for example, 5-200 mg of the compound of formula I or an equivalent amount of a pharmaceutically acceptable salt thereof.

The compositions may be obtained by conventional procedures using pharmaceutically acceptable diluents and carriers well known in the art. Tablets and capsules for oral administration may conveniently be formed with an enteric coating (such as one based on cellulose acetate phthalate) to minimise the contact of the active ingredient of formula I with stomach acids.

The compositions of the invention may also contain one or more agents known to be of value in the diseases or conditions of the cardiovasculature intended to be treated. Thus, they may contain, in addition to the compound of formula I, for example: a known platelet aggregation inhibitor, prostanoid constrictor antagonist or synthase inhibitor (thromboxane $A_2$ antagonist or synthase inhibitor), cyclooxygenase inhibitor, hypolipidemic agent, anti-hypertensive agent, inotropic agent, beta-adrenergic blocker, thrombolytic agent or a vasodilator.

In addition to their use in therapeutic medicine, the compounds of formula I are also useful as pharmacological tools in the development and standardisation of test systems for the evaluation of new cardiovascular agents in laboratory animals such as cats, dogs, rabbits, monkeys, rats and mice.

The invention will now be illustrated by the following non-limiting Examples in which, unless otherwise stated:

(i) evaporations were carried out by rotary evaporation in vacuo;

(ii) operations were carried out at room temperature, that is in the range 18°–26° C.;

(iii) flash column chromatography or medium pressure liquid chromatography (MPLC) was performed on silica gel [either Fluka Kieselgel 60 (catalogue no. 60738) obtained from Fluka AG, Buchs, Switzerland, or Merck Kieselgel Art. 9385, obtained from E Merck, Darmstadt, Germany];

(iv) yields are given for illustration only and are not necessarily the maximum attainable by diligent process development;

(v) proton NMR spectra were normally determined at 200 MHz in deuterated dimethyl sulphoxide as solvent, using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; q, quartet; and (vi) all end-products were characterised by microanalysis, NMR and/or mass spectroscopy.

EXAMPLE 1

7-amino-2-(2-furyl)-5-[2-(4-hydroxyphenyl)ethyl]amino[1,2,4]-triazolo[1,5-a][1,3,5]triazine (0.91 g) and 1,8-diazabicyclo[5,4,0]undec-7-ene (DBU, 0.37 ml) were added to a suspension of 7-amino-2-(2-furyl)-5-methylsulphonyl-[1,2,4]triazolo[1,5-a][1,3,5]triazine (0.82 g) in acetonitrile (50 ml) and the resulting mixture was heated under reflux for 17 hours, after which time thin layer chromatography (TLC) analysis on silica plates (eluent: methylene chloride-methanol 19:1 v/v) indicated that no methanesulphonyl starting material remained. The solvent was then evaporated and the residue was purified by column chromatography on silica (75 g) eluting with ethyl acetate-methylene chloride 7:3 v/v. A white solid was obtained, and this was crystallised from isopropanol to afford 7-amino-5-[4-(2-[7-amino-2-(2-furyl)-[1,2,4]triazolo[1,5-a][1,3,5]triazin-5-ylamino]ethyl)phenoxy]-2-(2-furyl)[1,2,4]triazolo[1,5-a][1,3,5]triazine, m.p. 285°–289° C.; microanalysis, found: C, 54.1; H, 4.4; N, 30.8%; $C_{24}H_{19}N_{13}O_3$ 1.0($C_3H_7OH$) requires: C, 54.2; H, 4.5; N, 30.5%; NMR: 2.92 (t, 2H, phenyl-$CH_2$), 3.55 (q, 2H, $CH_2$-N), 6.67 (m, 2H, 2 furyl-4H), 7.0 (d, 1H, furyl-3H), 7.11 (d, 1H, furyl-3'H), 7.16 and 7.35 ($A_2B_2$ pattern, 4H, phenyl-H), 7.5 (br t, 1H, NH rotamers), 7.85 (d, 1H, furyl-5H), 7.89 (d, 1H, furyl-5'H), 8.12 (br s, 2H, $NH_2$) and 8.93 (d, 2H, $NH_2$); m/e $(M+H)^+$ 538.

The necessary starting material was prepared as follows:

(1) Hydrogen chloride gas (20.0 g) was bubbled into an ice-cooled mixture of 2-furonitrile (46.5 g) and absolute ethanol (23.0 g). After addition of the gas, solid crystallised from the mixture. The crystalline solid was collected by filtration and heated in pyridine (300 ml) with aminoguanidine nitrate (56.0 g) under reflux for 4 hours. The mixture was cooled, solid material removed by filtration and the filtrate evaporated to give crude 3-amino-5-(2-furyl)-1,2,4-triazole. This material was purified by treatment with nitric acid (400 ml of 50% v/v). The crystalline salt which formed was collected by filtration, washed sequentially with water (100 ml) and ethanol (50 ml) and air dried to give 3-amino-5-(2-furyl)-1,2,4-triazole nitrate (45.0 g), m.p. 130°–133° C. (decomp.). Several batches (184.0 g) of this salt (184 g) were suspended in hot water (400 ml) and sodium carbonate (46.0 g) was added in portions. The basic solution obtained was allowed to cool to give 3-amino-5-(2-furyl)-1,2,4-triazole (82.0 g) as colourless prisms, m.p. 204°–206° C.; NMR 6.05(s, 2H, $NH_2$), 6.6(s, 1H, furyl-4H), 6.7(s, 1H, furyl-3H), 7.7(s,1H, furyl-5H), 12.05(br s,1H, NH).

(2) An intimate mixture of 3-amino-5-(2-furyl)-1,2,4-triazole (33.0 g) and dimethyl N-cyanodithioiminocarbonate (33.0 g) was heated at 170° C. for 1 hour, under a slow stream of argon. After cooling, the resulting solid was purified by column chromatography on silica (600 g) eluting with an increasing amount of ethyl acetate in dichloromethane (5–10% v/v) to give 7-amino-2-(2-furyl)-5-methylthio-[1,2,4]triazolo[1,5-a][1,3,5]triazine as a colourless solid (11.1 g), essentially pure by TLC, which was used without further purification. [A small amount of the above solid was recrystallised from ethanol to give, crystals, m.p. 238°–240° C.; microanalysis, found: C,44.0; H,3.3; N,33.7; $C_9H_8N_6SO$. 0.05$C_2H_5OH$ requires C,43.6; H,3.3; N,33.6; NMR 1.05 and 3.4 (t+q, ethanol of crystallisation), 2.5 (s, 3H, $CH_3S$—), 6.7(dd, 1H, furyl-4H), 7.2(d, 1H, furyl-3H), 7.7(d, 1H, furyl-5H) 8.7–9.0(br d, 2H, $NH_2$); m/e 248 $(M+)$.

(3) A solution of 3-chloroperoxybenzoic acid (50% strength, 45.0 g) in dichloromethane (300 ml) was added to a stirred, ice-cooled suspension of 7-amino-2-(2-furyl)-5-methylthio-[1,2,4]triazolo[1,5-a][1,3,5]triazine (8.0 g) in dichloromethane (300 ml). The residual aqueous layer was discarded. The resulting suspension was allowed to warm to ambient temperature and stirred for 16 hours. The solvent was evaporated and ethanol (150 ml) was added to the residue. The suspension obtained was left to stand for 30 minutes with occasional swirling. The solid was then collected by fitration, washed with ethanol and dried to give 7-amino-2-(2-furyl)-5-methylsulphonyl-[1,2,4]triazolo[1,5-a][1,3,5]triazine (6.6 g) as colourless solid, NMR: 3.3(s, 3H, $CH_3.SO_2$), 6.7(q, 1H, furyl-4H), 7.3(q, 1H, furyl-3H), 7.9(q, 1H, furyl-5H), 9.4–9.8(d, 2H, $NH_2$), which was used without further purification.

(4) 4-(2-Aminoethyl)phenol (2.74 g) was added to a stirred suspension of 7-amino-2-(2-furyl)-5-methylsulphonyl-[1,2,4]triazolo[1,5-a][1,3,5]triazine (1.4 g) in acetonitrile (150 ml) and stirring was continued overnight. The solvent was evaporated and the residue was purified by chromatography on silica (100 g) eluting with dichloromethane containing methanol (50% v/v). The solid (1.23 g) obtained was crystallised from ethyl acetate to give 7-amino-2-(2-furyl)-5-[2-(4-hydroxyphenyl)ethyl]amino-[1,2,4]triazolo[1,5-a][1,3,5]triazine, m.p. 225°–227° C.; microanalysis, found: C, 56.7; H, 4.6; N, 29.4%; $C_{16}H_{15}N_7O_2$ requires C, 57.0; H, 4.5; N, 29.1%; NMR: 2.73(t, 2H, $CH_2Ar$), 3.41(t, 2H, $NHCH_2$), 6.66(complex, 3H, 2 phenyl-H and furyl-4H), 7.02(complex, 3H, 2 phenyl-H and furyl-3H), 7.40(br t, 1H, —NH—), 7.82(q, 1H, furyl-5H), 8.0–8.4(br d, 2H, $NH_2$) and 9.1(s, 1H, OH); m/e 333 $(M+H)^+$.

EXAMPLE 2

Using a procedure similar to that described in Example 1, but using 7-amino-2-(2-furyl)-5-methylsulphonyl/pyrazolo[2,3-a][1,3,5]triazine and 1,2-dimethoxyethane as solvent; there was obtained 7-amino-5-[4-(2-[7-amino-2-(2-furyl)-[1,2,4]triazolo[1,5-a][1,3,5]triazin-5-ylamino]ethyl)phenoxy]-2-(2-furyl)pyrazolo[2,3-a][1,3,5]triazine, as a solid 198°–202° (decomp); microanalysis, found: C, 55.6; H, 4.4; N 29.0% $C_{25}H_{20}N_{12}O_3$ 1.0 $(C_2H_5OH)$ requires: C, 55.6; H, 4.5; N 28.9%; NMR: 2.90 (t, 2H, phenyl-$CH_2$), 3.50 (m, 2H, $CH_2$-N), 6.39 (s, 1H, pyrazole-3H), 6.64 (m, 2H, 2 furyl-4H); 6.97 (d, 1H, furyl-3H), 7.05 (d, 1H, furyl-3'H), 7.13 and 7.31 ($A_2B_2$ pattern, 4H, phenyl-H), 7.50 (br t, 1H, NH rotamers), 7.60 (m, 1H, furyl-5H), 7.85 (m, 1H, furyl-5'H), 8.12 (br s, 2H, $NH_2$) and 8.4–8.8 (d, 2H, $NH_2$); m/e $(M+H)^+$ 537.

The necessary starting material was prepared as follows:

(1) An intimate mixture of 3-amino-5-(2-furyl)-pyrazole (3.0 g; obtainable from the Maybridge Chemical Company Ltd., Tintagel, Cornwall) and dimethyl N-cyanodithioiminocarbonate (3.2 g) was heated at 180° C. for 5 minutes. The reaction mixture was cooled and the solid which formed was crystallised from ethanol to give 7-amino-2-(2-furyl)-5-methylthio-pyrazolo[2,3-a][1,3,5]triazine as a colourless crystalline solid, m.p. 234°–236° C.; microanalysis, found: C, 48.9; H, 3.7; N, 28.0%; $C_{10}H_9N_5OS$ requires: C, 48.6; H, 3.6; N, 28.3%; NMR: 2.5 (s, 3H, $CH_3S$), 6.5 (s, 1H, pyrazole-3H), 6.7 (q, 1H, furyl-4H), 7.0 (q, 1H, furyl-3H), 7.8 (q, 1H, furyl-5H), 8.2–8.7 (br d, 2H, $NH_2$); m/e 247 $(M^+)$.

(2) To a cooled suspension of 7-amino-2-(2-furyl)-5-methylthiopyrazolo[2,3-a]-1,3,5-triazine (4.3 g) in dichloromethane (50 ml) was added a solution of 3-chloroperoxybenzoic acid (15 g, 50% w/w) in dichloromethane (100 ml), discarding the aqueous layer. The reaction mixture was allowed to warm to ambient temperature and stirred for 16 hours. The solvent was removed in vacuo and the residue was triturated with ethanol. The solid formed was collected by filtration, washed with ethanol and dried to give an off-white solid (19.4 g). This material was crystallised from ethanol to give 7-amino-2-(2-furyl)-5-methylsulphonyl-pyrazolo[2,3-a][1,3,5]triazine as a crystalline solid, m.p. 215°–219° C.; microanalysis, found: C, 42.9; H, 3.4; N, 24.7%; $C_{10}H_9N_5O_3S$ requires: C, 43.0; H, 3.2; N, 25.0%; NMR, 3.3 (s, 3H, $CH_3SO_2$—), 6.6 (d, 1H, furyl-4H), 6.8 (s, 1H, pyrazole-3H), 7.1 (d, 1H, furyl-3H), 7.7 (d, 1H, furyl-5H); m/e 280 $(M+H^+)$.

EXAMPLE 3

Using a method similar to that described in Example 1 but using 7-amino-2-(2-furyl)-5-[2-(4-hydroxyphenyl)ethyl]aminopyrazolo[2,3-a][1,3,5]triazine and 7-amino-2-(2-furyl)-5-methylsulphonyl-pyrazolo[2,3-a][1,3,5]triazine in 1,2-dimethoxyethane as solvent; there was obtained 7-amino-5-[4-(2-[7-amino-2-(2-furyl)pyrazolo[2,3-a][1,3,5]triazin-5-ylamino]ethyl)-phenoxy]-2-(2-furyl)pyrazolo[2,3-a][1,3,5]triazine, as a solid mp 235°–8° C. (decomp); microanalysis, found: C, 57.9; H, 4.1; N 28.4% $C_{26}H_{21}N_{11}O_3$ requires: C, 58.3; H, 3.95; N 28.8%; NMR 2.88 (t, 2H phenyl-$CH_2$), 3.51 (m, 2H, $CH_2$-N), 6.08 (s, 1H, pyrazole-3H), 6.39 (s, 1H, pyrazole-3'H), 6.62 (m, 2H, 2 furyl-4H), 6.90 (d, 1H, furyl-3H), 6.97 (d, 1H, furyl-3'H), 7.12 and 7.30 ($A_2B_2$ pattern, 4H, phenyl-H), 7.77 (m, 1H, furyl-5H) 7.81 (m, 1H, furyl-5'H) and 8.36–8.56 (d, 2H, $NH_2$); m/e $(M+H)^+$ 536.

The necessary starting material was prepared as follows:

4-(2-aminoethyl)phenol (1.37 g) was added to a stirred suspension of 7-amino-2-(2-furyl)-5-(methylsulphonyl)pyrazolo[2,3-a][1,3,5]triazine (1.4 g) in acetonitrile (150 ml) and the mixture was heated under reflux for 6 hours. The solvent was removed in vacuo and the residue was purified by chromatography on silica (100 g) eluting with dichloromethane containing methanol (5.0% v/v). The solid obtained was crystallised from ethanol to give 7-amino-2-(2-furyl)-5-[2-(4-hydroxyphenyl)ethyl]amino-pyrazolo[2,3-a][1,3,5]triazine as a crystalline solid (0.36 g), m.p. 213°–215° C.; microanalysis, found: C, 60.0; H, 5.3; N, 24.0%; $C_{17}H_{16}N_6O_2$ 0.3$C_2H_5OH$ requires C, 60.2; H, 5.2; N, 24.0% NMR: 1.05 (t, $CH_3CH_2OH$), 2.70 (t, 2H, $CH_2Ar$), 3.4 (complex, $NCH_2$ and $CH_3CH_2OH$), 4.31 (t, $CH_3CH_2OH$), 6.08 (s, 1H, pyrazole-3H), 6.62 (dd, 1H, furyl-4H), 6.7 and 7.05 ($A_2B_2$ pattern, 4H, phenyl-H), 6.86 (t, 1H, NH), 6.92 (d of d, 1H, furyl-3H), 7.8 (br s, 2H, $NH_2$) and 9.12 (s, 1H, OH); m/e 337 $(M+H)^+$.

EXAMPLE 4

Using a procedure similar to that described in Example 1 but using 7-amino-2-(2-furyl)-5-methylsulphonyl[1,2,4]triazolo[1,5-a][1,3,5]triazine and 7-amino-2-(2-furyl)-5-[2-(4-hydroxyphenyl)ethyl]aminopyrazolo[2,3-a][1,3,5]triazine un 1,2-dimethoxyethane as solvent; there was obtained 7-amino-5-[4-(2-[7-amino-2-(2-furyl)pyrazolo[2,3-a][1,3,5]triazin-5-ylamino]ethyl)phenoxy]-2-(2-furyl)-[1,2,4]-triazolo[1,5-a][1,3,5]triazine, m.p. 298°–301° C. (decomp); microanalysis, found: C, 55.4, H, 3.8; N, 30.8; $H_2O$ 1.0% $C_{25}H_{20}N_{12}O_3$ 0.33($H_2O$) requires C, 55.3; H, 3.8, N, 30.9; $H_2O$, 1.1%; NMR: 2.89 (t, 2H, phenyl-$CH_2$), 3.51 (q, 2H, $CH_2$-N), 6.1 (s, 1H, pyrazole-3H), 6.62 (d of d, 1H, furyl-4H), 6.69 (d of d, 1H, furyl-4'H), 6.91 (d, 1H, furyl-3H), 6.98 (t, 1H, NH,$CH_2$), 7.11 (d, 1H, furyl-3'H) 7.15 and 7.33 ($A_2B_2$ pattern, 4H, phenyl-H), 7.78 (d, 1H, furyl-5H), 7.82 (br, 2H, $NH_2$), 7.90 (d, 1H, furyl-5'H) and 8.80–9.06 (d, 2H, $NH_2$); m/e $(M+H)^+$ 537.

EXAMPLE 5

Using a procedure similar to that described in Example 1 but using 7-amino-2-(2-furyl)-5-methylsulphonyl-pyrazolo[2,3-a][1,3,5]triazine and 7-amino-2-(2-furyl-5-[2-(3-hydroxyphenyl)ethyl]amino[1,2,4]triazolo[1,5-a][1,3,5]-triazine in 1,2-dimethoxyethane as solvent; there was obtained 7-amino-5-[3-(2-[7-amino-2-(2- furyl)-[1,2,4]triazolo[1,5-a][1,3,5]triazin-5-ylamino]ethyl)phenoxy]-2-(2-furyl)-pyrazolo[2,3-a][1,3,5]triazine as a solid m.p. 248°–251° C. (decomp); microanalysis found: C, 55.0; H, 3.4; N, 30.4; $H_2O$, 1.7%; $C_{25}H_{20}N_{12}O_3$ (0.5) $H_2O$ requires: C, 55.0; H, 3.8; N, 30.4; $H_2O$, 1.65%; NMR: 2.60 (t, 2H, phenyl-$CH_2$), 3.55 (q, 2H, $CH_2N$), 6.41 (s, 1H, pyrazole-3H), 6.65 (m, 2H, furyl-4H), 6.99 (d, 1H, furyl-3H), 7.04 (d, 1H, furyl-3'H), 7.05–7.45 (complex, 4H, phenyl-H), 7.48 (t, 1H, $NHCH_2$), 7.81 (d, 1H, furyl-5H), 7.84 (d, 1H, furyl-5'H), 8.12 (br s, 2H, $NH_2$) and 8.4–8.78 (d, 2H, $NH_2$); m/e $(M+H)^+$ 537.

The necessary starting material was prepared as follows:

Using a procedure similar to that described in Example 1, part (4), but using 3-(2-aminoethyl)phenol, there was obtained 7-amino-2-(2-furyl)-5-[2-(3-hydroxyphenyl)ethyl]amino-[1,2,4]triazolo[1,5-a][1,3,5]triazine, m.p. 190°–193° C.; microanalysis, found C, 57.3; H, 4.4; N, 29.2%; $C_{16}H_{15}N_7O_2$ requires: C, 57.0; H, 4.4; N, 29.1%; NMR: 2.76 (t, 2H, phenyl-$CH_2$); 3.46 (m, 2H, $CH_2N$), 6.65 (m, 1H, furyl-4H), 6.5–7.2 (complex, 4H, phenyl-H), 7.04 (d, 1H, furyl-3H), 7.43 (t, 1H, NH), 7.85 (d, 1H, furyl-5H), 8.1 (br s, 2H, $NH_2$) and 9.24 (s, 1H, OH); m/e 338 $(M+H)^+$.

EXAMPLE 6

Using a procedure similar to that described in Example 1 but using 7-amino-2-(2-furyl)-5-[2-(4-hydroxyphenyl)methyl]amino[1,2,4]-triazolo[1,5-a][1,3,5]triazine in 1,2 dimethoxyethane as solvent; there was obtained 7-amino-5-[4-(2-[7-amino-2-(2-furyl)[1,2,4]-triazolo[1,5-a][1,3,5]triazin-5-ylamino]methyl)phenoxy]-2-(2-furyl)-[1,2,4]triazolo[1,5-a][1,3,5]triazine, m.p. 228°–232.5° C. (decomp), microanalysis, found C, 52.9; H, 3.6; N, 32.9%; $C_{23}H_{17}N_{13}O_3$ (0.5)$C_3H_7OH$ requires: C, 53.1; H, 3.8; N, 32.9%; NMR: 4.55 (m, 2H, phenyl-$CH_2$), 6.66 (m, 2H, furyl-4H and furyl-4'H), 7.03 (d, 1H, furyl-3H), 7.11 (d, 1H, furyl-3'H), 7.15 and 7.39 ($A_2B_2$ pattern, 4H, phenyl-H), 7.84 (m, 1H, furyl-5H), 7.89 (m, 1H, furyl-5'H), 8.02 (t, 1H, $CH_2NH$), 8.17 (br s, 2H, $NH_2$) and 8.8–9.08 (d, 2H, $NH_2$).

The starting material was prepared as follows:

(1) 4-Benzyloxy-benzylamine (1.6 g) was added to a stirred suspension of 7-amino-2-(2-furyl)-5-methylsulphonyl-[1,2,4]triazolo[1,5-a][1,3,5]triazine (1.0 g) in acetonitrile (50 ml) and the mixture refluxed on a steambath for 2.5 hours. The solvent was evaporated and the residue was purified by chromatography on silica (125 g) eluting with dichloromethane containing methanol (2% v/v). The residual solid was crystallised from ethanol and gave 7-amino-5-[(4-benzyloxyphenyl)methyl]amino-2-(2-furyl)-[1,2,4]triazolo[1,5-a][1,3,5]triazine m.p. 168°–70° C.; microanalysis, found: C, 63.9; H, 4.6; N, 23.2% $C_{22}H_{19}N_7O_2$ (0.1) $C_2H_5OH$ requires C, 63.7; H, 4.7; N, 23.4% NMR: 4.44 (d, 2H, $NHCH_2$), 5.07 (s, 2H, $CH_2O$); 6.65 (d of d, 1H, furyl-4H), 6.94 and 7.25 ($A_2B_2$ pattern, 4H, phenyl-H), 7.04 (d, 1H, furyl-3H), 7.3–7.5 (complex, 6H, phenyl-H and NH), 7.84 (d, 1H, furyl-5H) and 8.14 (br s, 2H, $NH_2$); m/e 414 $(M+H)^+$.

(2) A solution of 7-amino-5-[(4-benzyloxyphenyl)methyl]amino-2-(2-furyl)-[1,2,4]triazolo[1,5-a][1,3,5]triazine (2.37 g) in ethyl acetate (150 ml) and methanol (150 ml) was treated with 10% palladium on carbon (3.0 g) and hydrogenated at atmospheric pressure for 2.5 hours. The catalyst was filtered through diatomaceous earth and the liquors evaporated. The residue was purified by chromatography on silica (100 g) eluting with dichloromethane containing methanol 3–30% v/v, and gave 7-amino-2-(2-furyl)-5-[(4-hydroxyphenyl)methyl]amino-[1,2,4]-triazolo[1,5-a][1,3,5]triazine, m.p. 268–270; NMR: 4.39 (d, 2H, $CH_2N$), 6.64 (d of d, 1H, furyl-4H), 6.68 and 7.13 ($A_2B_2$ pattern, 4H, phenyl-H), 7.03 (d, 1H, furyl-3H), 7.8 (t, 1H, NH), 7.84 (d, 1H, furyl-5H), 8.13 (br s, 2H, $NH_2$) and 9.19 (s, 1H, OH); m/e 324 $(M+H)^+$.

EXAMPLE 7

Using a procedure similar to that described in Example 1 but using 7-amino-2-(2-furyl)-5-[2-(3-hydroxyphenyl)ethyl]amino-[1,2,4]triazolo[1,5-a][1,3,5]triazine and 1,2-dimethoxyethane as solvent; there was obtained 7-amino-5-[4-(2-[7-amino-2-(2-furyl)-[1,2,4]triazolo[1,5-a][1,3,5]triazin-5-ylamino]ethyl)phenoxy]-2-(2-furyl)[1,2,4]triazolo[1,5-a][1,3,5]triazine m.p. 186°–190° C.; microanalysis, found: C, 53.4; H, 3.8; N, 33.1%; $C_{24}H_{19}N_{13}O_3$), 0.25 ($C_2H_5OH$) requires: C, 53.5; H, 3.75; N, 33.1%; NMR: 2.91 (t, 2H, phenyl-$CH_2$), 3.52 (m, 2H, $CH_2N$), 6.65 (m, 1H, furyl-4H), 6.69 (m, 1H, furyl-4'H), 7.05 (m, 1H, furyl-3H), 7.11 (m, 1H, furyl-3'H), 7.10–7.44 (complex, 4H, phenyl-H), 7.5 (t, 1H, $CH_2NH$), 7.84 (d, 1H, furyl-5H), 7.89 (d, 1H, furyl-5'H), 8.1 (br s, 2H, $NH_2$) and 8.8–9.07 (d, 2H, $NH_2$); m/e $(M+H)^+$ 538.

EXAMPLE 8

Using a procedure similar to that described in Example 1 but using 7-amino-2-(2-furyl)-5-methylsulphonyl[1,2,4]triazolo[1,5-a][1,3,5]triazine and 7-amino-2-(2-furyl)-5-[2-(2-hydroxyphenyl)ethyl]aminopyrazolo[2,3-a][1,3,5]triazine in 1,2-dimethoxyethane as solvent, there was obtained 7-amino-5-[2-(2-[7-amino-2-(2-furyl)-pyrazolo[2,3-a][1,3,5]triazin-5-ylamino]ethyl)-phenoxy]-2-(2-furyl)-[1,2,4]triazolo[1,5-a][1,3,5]triazine, m.p. 185°–88° C. (decomp); microanalysis, found: C, 53.9; H, 4.0; N, 30.3; $H_2O$, 3.3% $C_{25}H_{20}N_{12}O_3.H_2O$ requires: C, 54.1; H, 4.0; N, 30.3; $H_2O$, 3.25%; NMR: 2.81 (t, 2H, phenyl-$CH_2$), 3.46 (m, 2H, $CH_2N$), 5.92 (s, 1H, pyrazole-3H), 6.59 (d of d, 1H, furyl-4H), 6.67 (d of d, 1H, furyl-4'H), 6.85 (d, 1H, furyl-3H), 7.10 (d, 1H, furyl-3'H) 7.1–7.5 (complex, 4H,phenyl-H) 7.74 (d, 1H, furyl-5H), 7.88 (d, 1H, furyl-5'H) and 8.83–9.08 (d, 2H, $NH_2$); m/e $(M+H)^+$ 537.

The starting material was prepared as follows:

(1) Using a procedure similar to that described in Example 1, part (4), but using 2-(2-benzyloxyphenyl)ethylamine there was obtained 7-amino-5-[2-(2-benzyloxyphenyl)ethyl]amino-2-(2-furyl)-[1,2,4]triazolo[1,5-a][1,3,5]triazine; m.p. 151°–153° C. microanalysis, found: C, 64.4; H, 4.8; N, 23.0; $C_{23}H_{21}N_7O_2$ requires: C, 64.6; H, 4.95; N, 22.9%; NMR: 2.90 (t, 2H, phenyl $CH_2$); 3.53 (m, 2H, $CH_2N$); 5.13 (s, 2H, $CH_2O$); 6.68 (d of d, 1H, furyl-4H), 7.04 (d, 1H, furyl-3H), 6.8–7.6 (complex, 9H, phenyl-H); 7.88 (s, 1H, furyl-5H) and 8.11 (br s, 2H, $NH_2$); m/e 428 $(M+H)^+$.

(2) A solution of the product of step (1) (0.9g) in methanol (150 ml) was hydrogenated at room-temperature and pressure using 10% palladium on carbon (0.9 g) catalyst. After the uptake of hydrogen was complete, the catalyst was filtered off and the solvent evaporated. The residue was crystallised from ethanol, and gave 7-amino-2-(2-furyl)-5-[2-(hydroxyphenyl)ethyl]amino-[1,2,4]triazolo[1,5-a][1,3,5]triazine, m.p. 260°–263° C. microanalysis, found: C, 57.2; H, 4.8; N, 28.6%; $C_{16}H_{15}N_7O_2$ (0.15) $C_2H_5OH$ requires: C, 57.0; H, 4.7; N, 28.5%; NMR: 2.81 (t, 2H, phenyl-H), 3.49 (m, 2H, CH₂N); 6.71 (d of d, 1H, furyl-4H), 7.03 (d, 1H, furyl-3H), 6.7-7.15 (complex, 4H, phenyl-H); 7.85 (m, 1H, NH); 7.84 (s, 1H, furyl-5H); 8.09 (br s, 2H, NH₂) and 9.31 (s, 1H, OH); m/e 338 (M+H)⁺.

EXAMPLE 9

Using a method similar to that described in Example 1 but using 7-amino-2-(2-furyl)-5-[2-(2-hydroxyphenyl)ethyl]amino pyrazolo[2,3-a]triazine and 7-amino-2-(2-furyl)-5-methylsulphonylpyrazolo[2,3-a][1,3,5]triazine in 1,2-dimethoxyethane as solvent; there was obtained 7-amino-5-[2-(2-[7-amino-2-(2-furyl)pyrazolo[2,3-a][1,3,5]triazin-5-ylamino]ethyl)phenoxy]-2-(2-furyl)-pyrazolo[2,3-a][1,3,5]triazine, as a solid m.p. 256°-259° C. (decomp); microanalysis, found: C, 56.5; N, 4.1; H, 27.7; H₂O, 2.8%, C₂₆H₂₁N₁₁O₃.H₂O requires: C, 56.5; H, 4.1; N, 27.9; H₂O, 3.2%; NMR: 2.80 (t, 2H, phenyl-CH₂), 3.50 (m, 2H, CH₂N), 5.92 (s, 1H, pyrazole-3H) 6.42 (s, 1H, pyrazole-3'H), 6.60 (d of d, 1H, furyl-4H), 6.64, (d of d, 1H, furyl-4'H), 6.87 (d, 1H, furyl-3H), 6.87 (br, 1H, CH₂NH), 6.98 (d, 1H, furyl-3'H), 7.1-7.5 (complex, 4H, phenyl-H), 7.74 (m, 1H, furyl-5H), 7.74 (br s, 2H, NH₂), 7.82 (m, 1H, furyl-5'H and 8.42-8.80 (d, 2H, NH₂); m/e (M+H)⁺ 536.

EXAMPLE 10

1,6-Hexanediamine (0.21 g) was added to a stirred suspension of 7-amino-2-(2-furyl)-5-methylsulphonyl-[1,2,4]triazolo[1,5-a][1,3,5]triazine (1.02 g) in acetonitrile (100 ml) and the stirring was continued for 18 hours. A solid was filtered off and purified by chromatography on silica-gel (150 g) eluting with dichloromethane containing methanol (10-50% v/v). The solid (0.4 g) obtained was crystallised from ethanol and gave N,N'-hexamethylene bis[N-7-amino-2-(2-furyl)-[1,2,4]triazolo[1,5-a][1,3,5]triazin-5-yl)amine] m.p. 265°-7° C. microanalysis, found: C, 48.7; H, 5.3; N, 36.0; H₂O, 3.6%; C₂₂H₂₄N₁₄O₂ (1.2) H₂O requires C, 49.1; H, 4.9; N, 36.4; H₂O 4.0%, NMR: 1.34 (complex, 4H, CH₂), 1.54 (complex, 4H, CH₂CH₂N), 3.27 (complex, CH₂N), 6.65 (d of d, 2H, furyl-4H), 7.03 (d, 2H, furyl-2H), 7.38 (t, 2H, CH₂NH), 7.83 (2H, furyl-5H) and 8.06 (br s, 4H, NH₂); m/e 517 (M+H)⁺.

EXAMPLE 11

The following illustrate representative pharmaceutical dosage forms containing a compound of formula I, for example as illustrated in any of the previous Examples, (hereafter referred to as "compound X"), for therapeutic or prophylactic use in humans:

| (a) Tablet | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (b) Capsule | mg/capsule |
|---|---|
| Compound X | 10 |
| Lactose Ph.Eur | 488.5 |
| Magnesium stearate | 1.5 |

The above formulations may be obtained by conventional procedures well known in the pharmaceutical art. The tablets may be enteric coated by conventional means, for example to provide a coating of cellulose acetate phthalate.

CHEMICAL FORMULAE

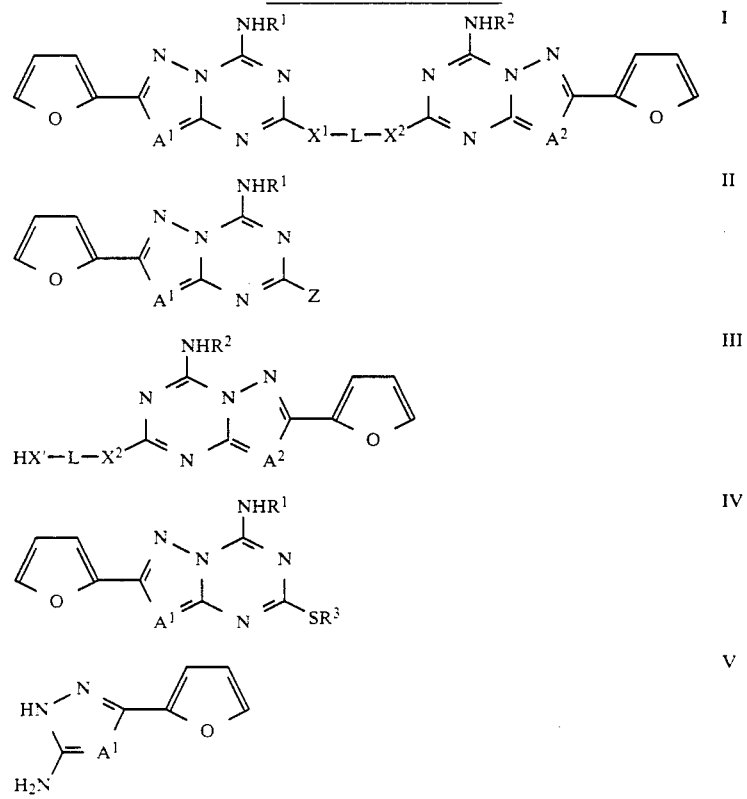

CHEMICAL FORMULAE

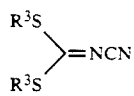

VI

What is claimed is:

1. A compound of the formula I

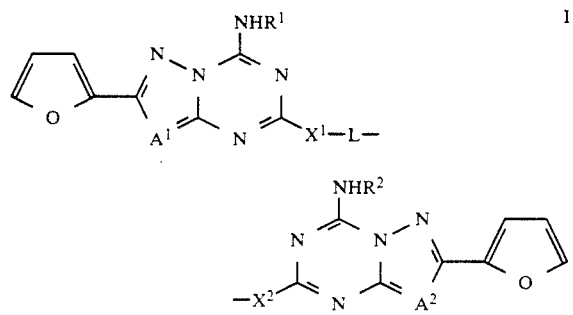

wherein:

$A^1$ and $A^2$ are each independently N or CT in which T is hydrogen or (1-4C)alkyl;

$R^1$ and $R^2$ are each independently hydrogen, (1-6C)alkyl, or (1-4C)alkanoyl;

$X^1$ and $X^2$ are each independently O, S or NH; and

L is a (3-7C)cycloalkylene group or a (1-8C)alkylene chain optionally interrupted or extended by a group selected from phenylene, phenyleneoxy or oxyphenyleneoxy, the phenylene portion of said group being unsubstituted or substituted by one of halogen, hydroxy and (1-4C)alkoxy, provided that all heteroatoms in the group $X^1$—L—$X^2$ are separated from one another by at least two carbon atoms; or a pharmaceutically acceptable salt thereof.

2. A compound as claimed in claim 1, in which $R^1$ and $R^2$ are both hydrogen.

3. A compound as claimed in claim 1 or claim 2, in which $A^1$ and $A^2$ are independently N or CH.

4. A compound as claimed in claim 1 or claim 2, in which one of $X^1$ and $X^2$ represents NH and the other represents O or NH.

5. A compound as claimed in claim 1 or claim 2, in which L represents a cyclopentylene or cyclohexylene group, or methylene, ethylene, propylene, methylethylene, butylene, dimethylethylene, pentylene or hexylene optionally interrupted or extended by a phenylene, phenyleneoxy or oxyphenyleneoxy group.

6. A compound as claimed in claim 5, in which L is ethylenephenyleneethylene, ethylenephenyleneoxyethylene, ethyleneoxyphenyleneoxyethylene, phenylenemethylene, phenyleneethylene or phenyleneoxyethylene, the phenylene portion of any of which may be unsubstituted or substituted by one of halogen, hydroxy and (1-4C)alkoxy.

7. A compound as claimed in claim 1, in which $R^1$ and $R^2$ are both hydrogen;

$A^1$ and $A^2$ are each independently N or CH;

$X^1$ is O;

$X^2$ is S or NH; and

L is a phenylene(1-3C)alkylene or phenyleneoxy(2-3C)alkylene group, the phenylene portion of said group being unsubstituted or substituted by one of halogen, hydroxy and (1-4C)alkoxy; and pharmaceutically acceptable salts thereof.

8. A pharmaceutical composition, which comprises a compound of formula I or a pharmaceutically acceptable salt thereof as defined in claim 1 and a pharmaceutically acceptable diluent or carrier.

9. A method of antagonising one or more of the actions of adenosine in a warm-blooded animal requiring such treatment by administering an effective amount of a compound of formula I as defined in claim 1, or a pharmaceutically acceptable salt thereof.

* * * * *